US011319232B2

(12) United States Patent
Grison

(10) Patent No.: US 11,319,232 B2
(45) Date of Patent: May 3, 2022

(54) TREATMENT OF QUARRY LIQUID EFFLUENT

(71) Applicant: CENTRE NATIONAL DE LA RECHERCHE SCIENTIFIQUE, Paris (FR)

(72) Inventor: Claude Grison, Grabels (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/499,097

(22) PCT Filed: Mar. 30, 2018

(86) PCT No.: PCT/EP2018/058358
§ 371 (c)(1),
(2) Date: Sep. 27, 2019

(87) PCT Pub. No.: WO2018/178371
PCT Pub. Date: Oct. 4, 2018

(65) Prior Publication Data
US 2020/0039856 A1 Feb. 6, 2020

(30) Foreign Application Priority Data

Mar. 31, 2017 (FR) ..................... 17 52822

(51) Int. Cl.
*C02F 9/00* (2006.01)
*B01J 23/00* (2006.01)
*B01J 23/02* (2006.01)
*B01J 23/06* (2006.01)
*B01J 23/10* (2006.01)
*B01J 23/26* (2006.01)
*B01J 23/34* (2006.01)
(Continued)

(52) U.S. Cl.
CPC ............... *C02F 9/00* (2013.01); *B01J 23/002* (2013.01); *B01J 23/007* (2013.01); *B01J 23/02* (2013.01); *B01J 23/06* (2013.01); *B01J 23/10* (2013.01); *B01J 23/26* (2013.01); *B01J 23/34* (2013.01); *B01J 23/40* (2013.01); *B01J 23/8892* (2013.01); *B01J 35/02* (2013.01); *B01J 37/031* (2013.01); *B01J 37/036* (2013.01); *B01J 37/06* (2013.01); *B01J 37/084* (2013.01); *B01J 37/086* (2013.01); *B01J 37/12* (2013.01); *B09C 1/08* (2013.01); *C01G 45/02* (2013.01); *C02F 1/74* (2013.01); *C07B 41/06* (2013.01); *C07C 45/298* (2013.01); *C07C 45/512* (2013.01); *C07D 307/46* (2013.01); *C07D 307/48* (2013.01); *C02F 1/004* (2013.01); *C02F 1/5245* (2013.01); *C02F 1/66* (2013.01); *C02F 1/722* (2013.01); *C02F 2101/206* (2013.01)

(58) Field of Classification Search
CPC .... C02F 9/00; C02F 1/74; C02F 1/004; C02F 1/5245; C02F 1/66; C02F 1/722; C02F 2101/206; B01J 23/002; B01J 23/007; B01J 23/02; B01J 23/26; B01J 23/40; B01J 23/8892; B01J 35/02; B01J 37/06; B01J 37/084; B01J 37/086; B01J 23/34; B01J 37/031; B01J 37/12; B01J 23/06; B01J 23/10; B01J 37/036; B01J 37/36; B01J 23/70; C07B 41/06; C07B 31/00; C07B 33/00; C07B 37/00; C07B 61/00; C01G 45/02; C07D 307/46; C07D 307/48; C07D 301/03; B09C 1/00; B09C 1/105; B09C 1/08; C07C 45/298; C07C 45/512; C07C 2531/00; C07C 1/00; C07C 2/00; C07C 9/00; C07C 45/00; C22B 11/042; C22B 11/048
See application file for complete search history.

(56) References Cited

U.S. PATENT DOCUMENTS 2,786,751 A    12/1958  Tuhin et al.
9,284,206 B2 *  3/2016  Presutti ................... C02F 9/00
(Continued)

FOREIGN PATENT DOCUMENTS

BE       573030 A      12/1958
EP      0333218 A2      9/1989
(Continued)

OTHER PUBLICATIONS

El Araby, R., S., "Treatment of iron and manganese in simulated groundwater via ozone technology." Desalination 249.3 (2009): 1345-1349.*
Cahiez, G.,"Manganese dioxide." Encyclopedia of reagents for organic synthesis (2001): 1-16.*
EWQA Conference, Hunt Valley Maryland (2014) p. 1-61.*
Zhang, W., "Investigation of methods for removal and recovery of manganese in hydrometallurgical processes." Hydrometallurgy 101. 1-2 (2010): 58-63.*
(Continued)

*Primary Examiner* — John M Mauro
(74) *Attorney, Agent, or Firm* — Nixon & Vanderhye

(57) ABSTRACT

Disclosed is a method for preparing a solid material including manganese, the method including the following steps: a. bringing into contact an aqueous effluent including manganese, for example at least 5 mg/L, typically at least 5 to 50 mg/L, and preferably 7 to 25 mg/L of manganese, with an oxidizing agent, manganese, preferably at a temperature between 10° C. and 50° C., and obtaining an oxidized aqueous solution; b. adding a base to the oxidized aqueous solution obtained at the end of step a) until a pH of between 8 and 12, preferably greater than 9, and preferably from 9 to 10.5, and obtaining a solution including a precipitate; c. filtration of the solution obtained at the end of step b); and d. obtaining a solid material including manganese, and especially manganese (IV) and/or Mn (III).

15 Claims, 1 Drawing Sheet

(51) Int. Cl.

| | | |
|---|---|---|
| *B01J 23/40* | (2006.01) | |
| *B01J 23/88* | (2006.01) | |
| *B01J 35/02* | (2006.01) | |
| *B01J 37/03* | (2006.01) | |
| *B01J 37/06* | (2006.01) | |
| *B01J 37/08* | (2006.01) | |
| *B01J 37/12* | (2006.01) | |
| *B09C 1/08* | (2006.01) | |
| *C01G 45/02* | (2006.01) | |
| *C02F 1/74* | (2006.01) | |
| *C07B 41/06* | (2006.01) | |
| *C07C 45/29* | (2006.01) | |
| *C07C 45/51* | (2006.01) | |
| *C07D 307/46* | (2006.01) | |
| *C07D 307/48* | (2006.01) | |
| *C02F 1/00* | (2006.01) | |
| *C02F 1/52* | (2006.01) | |
| *C02F 1/66* | (2006.01) | |
| *C02F 1/72* | (2006.01) | |
| *B01J 23/70* | (2006.01) | |
| *B09C 1/00* | (2006.01) | |
| *B09C 1/10* | (2006.01) | |
| *C07B 31/00* | (2006.01) | |
| *C07B 33/00* | (2006.01) | |
| *C07B 37/00* | (2006.01) | |
| *C07B 61/00* | (2006.01) | |
| *C07C 1/00* | (2006.01) | |
| *C07C 2/00* | (2006.01) | |
| *C07C 9/00* | (2006.01) | |
| *C07C 45/00* | (2006.01) | |
| *C07D 301/03* | (2006.01) | |
| *B01J 37/36* | (2006.01) | |
| *B01J 23/889* | (2006.01) | |
| *C02F 101/20* | (2006.01) | |

(56) References Cited

U.S. PATENT DOCUMENTS

| | | | |
|---|---|---|---|
| 2004/0094484 A1 | 5/2004 | Zhuang | |
| 2005/0217174 A1 | 10/2005 | Angle et al. | |
| 2011/0163042 A1 | 7/2011 | Kobayashi et al. | |
| 2013/0001173 A1* | 1/2013 | Kobayashi | C02F 1/66 210/722 |
| 2014/0124453 A1 | 5/2014 | Presutti | |

FOREIGN PATENT DOCUMENTS

| | | |
|---|---|---|
| EP | 1806177 A1 | 7/2007 |
| EP | 2504096 A1 | 10/2012 |
| EP | 2554256 A1 | 2/2013 |
| EP | 2769765 A1 | 8/2014 |
| EP | 2822684 A1 | 1/2015 |
| EP | 2874742 A1 | 5/2015 |
| EP | 3021963 A1 | 5/2016 |
| EP | 3260196 A1 | 12/2017 |
| EP | 3305405 A1 | 4/2018 |
| FR | 2987759 A1 | 9/2013 |
| FR | 2993480 A1 | 1/2014 |
| FR | 3008323 A1 | 1/2015 |
| FR | 3010329 A1 | 3/2015 |
| FR | 3023732 A1 | 1/2016 |
| FR | 3064497 A1 | 10/2018 |
| WO | 2006096472 A1 | 9/2006 |
| WO | 2007083304 A2 | 7/2007 |
| WO | 2011064462 A1 | 6/2011 |
| WO | 2011064487 A1 | 6/2011 |
| WO | 2013150197 A1 | 10/2013 |
| WO | 2014016509 A1 | 1/2014 |
| WO | 2014128283 A1 | 8/2014 |
| WO | 2015007990 A1 | 1/2015 |
| WO | 2015036714 A1 | 3/2015 |
| WO | 2016009116 A1 | 1/2016 |
| WO | 2016151261 A1 | 9/2016 |
| WO | 2017207947 A1 | 12/2017 |
| WO | 2018178371 A1 | 10/2018 |
| WO | 2018178374 A1 | 10/2018 |

OTHER PUBLICATIONS

Darmane, Y., "Preparation of chemical manganese dioxide from Moroccan pyrolusite mine waste." Hydrometallurgy 92.1-2 (2008): 73-78.*

International Search Report, dated Jul. 30, 2018, from corresponding PCT application No. PCT/EP2018/058358.

French Search Report, dated Jan. 19, 2018, from corresponding French application No. 1752822.

French Search Report, dated Jan. 24, 2018, from corresponding French application No. 1800053.

Feng et al.; Treatment of Acid Mine Water By Use of Heavy Metal Precipitation and Ion Exchange; Minerals Engineering; Pergamon Press; Jan. 1, 2000; pp. 623-642; vol. 13, No. 6; Oxford, United Kingdom.

Losfeld et al.; Design and performance of supported Lewis acid catalysts derived from metal contaminated biomass for Friedel-Crafts alkylation and acylation; Catalysis Today; ELSEVIER; Feb. 21, 2012; pp. 111-116; vol. 189, No. 1; Amsterdam, Netherlands.

Kastner et al.; Low Temperature Catalytic Oxidation of Hydrogen Sulfide and Methanethiol Using Wood and Coal Fly Ash; Environmental Science & Technology; Jun. 1, 2003; pp. 2568-2574; vol. 37, No. 11.

Kolar et al.; Low temperature catalytic oxidation of aldehydes using wood fly ash and molecular oxygen; Applied Catalysis B: Environmental; ELSEVIER; Oct. 29, 2007; pp. 203-217; vol. 76, No. 3-4; Amsterdam, Netherlands.

Kastner et al.; Catalytic ozonation of ammonia using biomass char and wood fly ash; Chemosphere; Pergamon Press; May 1, 2009; pp. 739-744; vol. 75, No. 6; Oxford, United Kingdom.

Abdel-Ghani et al.; Biosorption for Metal Ions Removal From Aqueous Solutions: A Review of Recent Studies; International Journal of Latest Research in Science and Technology; Jan. 1, 2014; pp. 24-42; vol. 3, No. 1.

* cited by examiner

TREATMENT OF QUARRY LIQUID EFFLUENT

BACKGROUND OF THE INVENTION

Field of the Invention

The present invention relates to a method for the preparation of a solid material comprising manganese as well as a method for the depollution of an effluent comprising manganese by bringing said effluent into contact with a manganese oxidizing agent.

The present invention also relates to a method of carrying out an organic synthesis reaction comprising the use of a material comprising manganese as a catalyst.

Description of the Related Art

Pyrite quarries are numerous in Europe and France, particularly in Normandy and Brittany, and are used, in particular, for the preparation of building materials. The runoff of rainwater in these quarries causes the oxidation of pyrite, which is mainly composed of iron disulfides. This transformation generates very acidic waters, at a pH of around 2.5-3, which are characterized by high concentrations of iron sulfate (typically between 5 and 45 mg/L). Manganese sulphate is also present in these acidic waters at a concentration of 5 to 50 mg/L. In order to meet discharge standards, industrial managers are currently treating effluents with soda or lime. This treatment is unsatisfactory since it generates a new waste in the form of basic sludge loaded with iron and manganese hydroxides which are stored on sites.

Thus, there is a need to provide a method for recovering an effluent comprising metals, preferably while avoiding the formation of basic sludge. In particular, there is a need to depollute effluents from pyrite quarries by controlled treatment, in order to meet the discharge standards imposed on industrialists.

SUMMARY OF THE INVENTION

An object of the present invention is therefore to provide a method for effectively removing effluents comprising metals.

Another object of the present invention is to provide a solid comprising at least manganese and that can be converted into manganese oxide, and used as a catalyst for oxidation reactions (alcohol oxidation, epoxidation, oxidative cleavage).

The present invention relates to a method P1 for preparing a solid material comprising manganese, said method comprising the following steps:
a. bringing into contact an aqueous effluent comprising manganese, for example at least 5 mg/L, typically at least 5 to 50 mg/L, preferably 7 to 15 mg/L of manganese, with a manganese oxidizing agent, preferably at a temperature between 10° C. and 50° C., and obtaining an oxidized aqueous solution;
b. adding to the oxidized aqueous solution obtained at the end of step a) of a base until a pH of between 8 and 12, preferably greater than 9, and preferably from 9 to 10.5, and obtaining a solution comprising a precipitate;
c. filtration of the solution obtained at the end of step b); and
d. obtaining a solid material comprising manganese, and especially manganese (IV) and/or Mn (III).

For the purposes of the present invention, the term "effluent" means an aqueous liquid medium, which may be chosen, for example, from effluents with metallic elements of extractive or industrial origin, for example originating from mines, quarries or the chemical industry, or the iron and steel industry. The effluent may also be derived from acid rock drainage, a leaching method or a method for preparing a metal catalyst. Advantageously, the effluent is a quarry effluent of pyrite.

In addition to manganese, the effluent may comprise at least one metal chosen from aluminum, calcium, copper, iron, potassium, magnesium, sodium, nickel, zinc, arsenic and silicon, preferably from aluminum, calcium, copper, iron, potassium, magnesium and sodium, wherein these metals are typically in their oxidized form. Advantageously, the effluent comprises from 5 to 50 ppm of manganese, from 2 to 180 ppm of aluminum, from 30 to 300 ppm of calcium, from 0 to 15 ppm of iron, from 2 to 20 ppm of potassium, from 30 to 250 ppm magnesium, 10 to 40 ppm sodium.

The metal content included in the effluent may be measured by Microwave Plasma-Atomic Emission Spectroscopy (MP-AES).

According to the present invention, the term "bringing into contact" is a step of adding the oxidizing agent in the effluent. Advantageously, step a) is carried out at ambient temperature. Preferably, step a) is carried out with stirring.

Advantageously, the oxidizing agent is chosen from hydrogen peroxide, dioxygen or sodium percarbonate, preferably the oxidizing agent is hydrogen peroxide ($H_2O_2$). $H_2O_2$ is an advantageous oxidizing agent since it is considered to be ecological ("green"), clean, inexpensive, easily available and non-hazardous at usual concentrations of use. Preferably, the oxidizing agent is added in a concentration of between 0.015 mL/L and 2 mL/L.

Preferably, the duration of step a) is between 1 min and 5 hours, preferably for 1 min and 1 hour, advantageously for 30 min. Typically, step a) is carried out at room temperature.

Preferably, in step b), the base is selected from potassium hydroxide, sodium hydroxide, calcium carbonate, sodium carbonate, or calcium hydroxide, while the base is preferably sodium hydroxide. Advantageously, during step b), the base is added until a pH of at least 9.5, preferably 9.5 is obtained.

Step c) may be carried out by any means known to those skilled in the art, for example by centrifugation. In addition to filtration, step c) may include washing the filtered solid material. This solid may be washed with water and/or ethanol. Once the solid is washed, it may be dried, for example for 24 hours at a temperature equal to 140° C.

Advantageously, the solid material obtained at the end of step d) comprises manganese, typically from 1 to 50% by weight, preferably from 1 to 20% by weight, more preferably from 2.5 to 13% by weight, of manganese. In addition to manganese, the solid material obtained at the end of step d) may comprise a metal chosen from aluminum, calcium, copper, iron, potassium, magnesium, sodium, zinc, nickel, arsenic and silicon, preferably from aluminum, calcium, copper, iron, potassium, magnesium and sodium. Advantageously, solid material obtained at the end of step d) comprises from 5 to 15% by weight of manganese, from 1 to 11% by weight of aluminum, from 1 to 7% by weight of calcium, from 0 to 5% by weight of iron, 0 to 1% by weight of potassium, 3 to 15% by weight of magnesium, and 0 to 1% by weight of sodium.

Advantageously, the solid material obtained at the end of step d) of the method P1 of the invention comprises oxides of manganese.

The present invention also relates to a method P2 for the depollution of an aqueous effluent comprising manganese, for example at least 5 mg/L, typically at least 5 to 50 mg/L, preferably 7 to 25 mg/L of manganese, and comprising the following steps:
 a. bringing into contact the aqueous effluent with a manganese oxidizing agent, preferably at a temperature between 10° C. and 50° C., and obtaining an oxidized aqueous solution;
 b. adding a base to the oxidized aqueous solution obtained at the end of step a) until a pH of between 8 and 12, preferably greater than 9, and preferably from 9 to 10.5, is achieved, and obtaining a solution comprising a precipitate;
 c. filtration of the solution obtained at the end of step b); and
 d. obtaining an aqueous effluent comprising less than 1 ppm, preferably less than 0.4 ppm of manganese.

All the embodiments, variants and preferred features of the method P1 apply, alone or in any of their combinations, also to the method P2 for the depollution of the invention.

Advantageously, the method P2 of the invention is applicable at the industrial level and meets the industrial standards of rejection imposed by European regulations. Preferably, the aqueous effluent obtained at the end of step d) comprises from 0 to 1 ppm of manganese, from 0 to 5 ppm of aluminum, from 40 to 250 ppm of calcium, from 0 to 2 ppm of iron, 3 to 10 ppm of potassium, 1 to 60 ppm of magnesium, 10 to 160 ppm of sodium.

Typically, the methods of the invention make it possible to avoid the formation of industrial sludge, and to consider that the effluents from the pyrite quarries are not waste but reaction media generating green oxidizing catalysts.

The present invention also relates to a solid material comprising manganese, and especially manganese (IV) and/or Mn (III), obtainable by the methods P1 or P2.

Advantageously, the manganese is integrated within a mineral matrix mainly composed of calcium hydroxide, magnesium hydroxide, calcium sulfate, aluminum hydroxide and calcium carbonate. This observation was made through MP-AES and IR analyses. In addition, XPS analyses made it possible to affirm the presence of different oxides of Mn (IV) and Mn (III). According to one variant, $Mn_2O_3$ is present in the mineral matrix. Morphology studies carried out using a high-resolution transmission electron microscope show that it is not a simple manganese dioxide, but an original material.

The solid material according to the invention is advantageously used as reagent or catalyst useful in green chemistry.

The inventors discovered an analogy between the structure of the sludge generated, i.e. a basic mixture of calcium and manganese, and the structure of the cluster $Mn_4CaO_5$. This cluster corresponds to the metallic center of the oxygen evolving complex (OEC) of water, the active site of photosystem II (PS II), an oxidoreductase that catalyses photooxidation of water in plants. This natural cluster has very interesting water oxidation properties.

The present invention also relates to a method P3 for implementing an organic synthesis reaction comprising the following steps:
 i) preparing a compound comprising manganese according to any one of methods P1 and P2 of the invention;
 ii) the implementation of an organic synthesis reaction by bringing into contact the compound obtained at the end of step i) as a catalyst with a reaction medium.

All the embodiments, variants, and preferred characteristics of the methods P1 and P2 also apply to the method P3, alone or in any of their combinations.

Surprisingly, it has been found that the compounds prepared via the methods P1 or P2 of the invention possess a better oxidizing power than that of the catalysts synthesized hitherto and known to those skilled in the art.

Advantageously, in the method P3 of the invention, the organic synthesis reaction is chosen from the oxidation reactions, preferably among
 the reactions for the oxidation of alcohols to aldehydes or ketones, of alcohols in alpha of an aromatic ring, including heterocyclic, in alpha of a double bond, aliphatic alcohols, for example oxidation of benzyl alcohol to benzaldehyde and selective oxidation of hydroxymethyl furfural to diformyl furan;
 the oxidative cleavage reactions, preferably the oxidative cleavage reactions of diols, of alpha hydroxy acids, of alpha hydroxylated carbonyl derivatives, of dicarbonyl derivatives; and
 the epoxidation reactions of alkenes, preferably from the epoxidation reactions of mono, di-, tri or tetrasubstituted alkenes.

Preferably, in the method P3 according to the invention, the organic synthesis reaction is carried out in the presence of an oxidizing agent for the catalyst, such as, for example, dioxygen in the air.

The invention will now be described by means of the following non-limiting examples.

DESCRIPTION OF THE PREFERRED EMBODIMENTS

Figure 1:
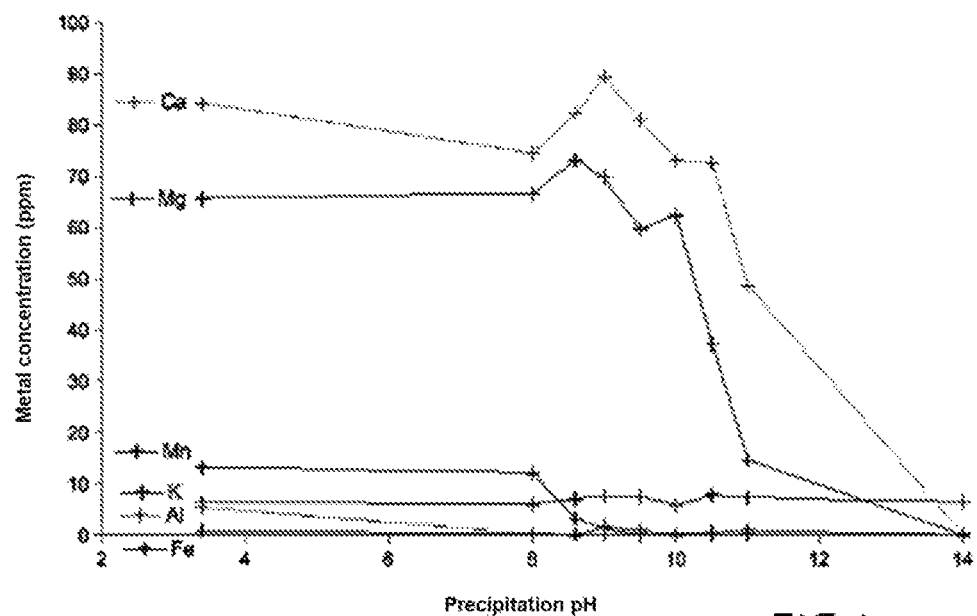
FIG. 1 shows the composition of the effluents according to the pH of precipitation of metals established by MP-AES

Example 1: Analysis of Effluents from Quarries of Pyrite

TABLE 1

MP-AES analyses of different effluents from pyrite quarries (values in ppm)

|  | Al | Ca | Cu | Fe | K | Mg | Mn | Na |
|---|---|---|---|---|---|---|---|---|
| Effluent 1 | 5.2 | 71.4 | 0.4 | 5.1 | 6.6 | 63.2 | 13.4 | 31.8 |
| Effluent 2 | 4.3 | 65.3 | 0.5 | 1.8 | 6.3 | 58.2 | 12.3 | 31.8 |
| Effluent 3 | 3 | 55.2 | 0.7 | 2.2 | 5.3 | 36.9 | 9.1 | 26.4 |
| Effluent 4 | 56.8 | 243.5 | 0.05 | 6.4 | 5.3 | 153.2 | 14.1 | 20.8 |
| Effluent 5 | 154 | 280 | <1 | 3.4 | 5.0 | 227 | 25.2 | 24.0 |

The effluents come from different pyrite quarries located in Brittany and Normandy. The effluent tested in the examples below is the effluent 3.

These analyses show that the effluents tested are characterized by a high content of manganese.

Example 2: Preparation of Compounds from Effluents

The effluent 3 (850 µL) was stirred with $H_2O_2$ (30%, 70 eq) at room temperature. After 30 min, NaOH (2 M) was added dropwise until the desired pH was reached. A black and then yellow precipitate appeared progressively as NaOH was added. The solution was stirred at room temperature for 1 night. The precipitated solid was filtered and washed with demineralized water (3 times) and then with absolute ethanol (3 times). The resulting solid, black (pH~9.5), dark brown (pH~10.5) or light brown (pH>11), was then dried at 140° C. for 24 hours.

The metal contents were measured by MP-AES and are presented in the following table.

TABLE 2

MP-AES analysis of Eco-PS2 formed at different precipitation pH.

| Compound | Precipitation pH | Mn (wt %) | Fe (wt %) | Ca (wt %) | Mg (wt %) | Na (wt %) | Al (wt %) | K (wt %) |
|---|---|---|---|---|---|---|---|---|
| 1 | 9.5 | 12.6 | 4.8 | 2.1 | 2.7 | 0.1 | 4.3 | 0. |
| 2 | 11 | 3.7 | 1.1 | 6.9 | 13.2 | 0.1 | 1.15 | 0.1 |
| 3 (comparative) | 14 | 2.8 | 0.3 | 14.4 | 13.2 | 0 | 1.0 | 0 |

The precipitation pH (step b) has a strong influence on the metal content in the final solid obtained after filtration.

Spectroscopic analysis (transmission electron microscopy) has shown that compounds 1 and 2 have a structure comprising "crumpled stars" without rods, whereas commercial compounds such as $MnO_2$ have a rod structure.

In addition, the XPS analyses suggest that the oxides of manganese (IV) present in the compounds 1 and 2 are associated with oxides of manganese (III). The presence of $Mn_2O3$ seems to be more plausible than that of manganite (γ-MnOOH). The XPS spectra of compounds 1 and 2 have a peak Mn 2p3/2 at 642.4 eV and a peak Mn 2p1/2 at 654.4 eV. The XPS analyses were carried out via a spectrophotometer ESCALAB 250 (Thermo Electron Corporation), equipped with a monochromatic Al Kα X-ray source (1486.6 eV).

XRD analyses show that only calcium sulphate is crystalline, while Mn oxides are amorphous, as the most active form of $MnO_2$. The XRD analyses were carried out via a BRUKER diffractometer (D8 advance, with a CuKα radiation λ=1.54086° A) equipped with a LynxEye detector.

Finally, the BET analyses show that the compound 1 is characterized by a specific surface area equal to 319 $m^2/g$ and an average pore diameter equal to 130 Å, while the compound 2 is characterized by a specific surface area equal to 154 $m^2/g$ and an average diameter of pores equal to 130 Å. Finally, BET analyses (Brunauer-Emmett-Teller method are established as follows: pore volume and average pore sizes are estimated from the Barrett-Joyner-Helenda method with the Kruk-Jaroniec-Sayari equation (BJH/KJS).

The addition of soda ash in the effluents is intended not only to neutralize the acidity of the water but also to precipitate all the metals present. Nevertheless, an excess of NaOH (up to pH=14). When the precipitation pH is 14, almost all of the calcium and magnesium contained in the effluents precipitates and the catalysts formed are then predominantly composed of the corresponding hydroxides. The latter can therefore modulate the activity of the compound, but also retain the reagents and/or products on the surface of the mineral matrix of the compound.

While calcium can have an activating effect on manganese, on the contrary, magnesium is described in the literature as having an antagonistic effect. It is therefore preferable to control the precipitation pH in order to selectively precipitate the metals.

The MP-AES analyses presented in FIG. 1 indicate that the manganese concentration in the effluents after metal precipitation is less than 1.8 ppm as soon as the pH reaches 9.

Figure 2:
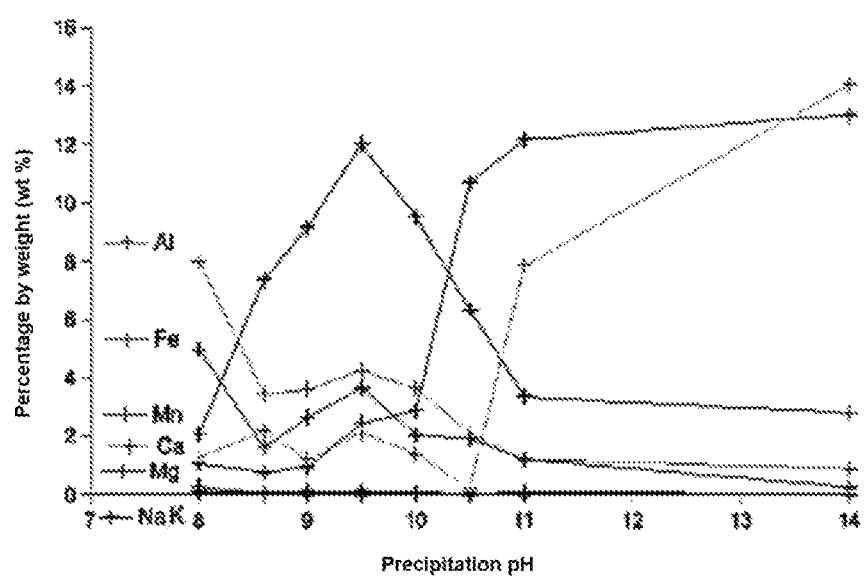
FIG. 2 shows the composition of the catalysts as a function of the precipitation pH established by MP-AES

Therefore, in order to meet the imposed industry standards, it is preferable that the precipitation pH be greater than 9. Then, the MP-AES analyses (FIG. 2) of the solids formed by varying the precipitation pH show that the highest manganese content is achieved for a pH of about 9.5, reaching about 13 wt %. Moreover, it should be noted that, in this case, the Mn/Ca molar ratio is very close to that of the natural cluster ($Mn_4$, Ca) derived from photosystem 2.

Example 3: Organic Synthesis Reaction

To test the activity of the materials of the invention, the oxidation of benzyl alcohol to benzaldehyde was taken as a model reaction.

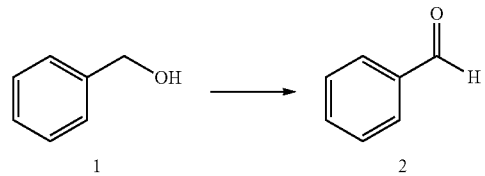 [SMILES: OCc1ccccc1 ; O=Cc1ccccc1]

The procedure adopted was as follows: the reagent (100 mmol·$L^{-1}$) was brought into contact with the solid prepared in Example 2 in anhydrous toluene and the solution was heated to 110° C. for 5 h. The reaction mixture was then analyzed by GC-MS to determine conversion and selectivity using dodecane as an internal standard.

The results obtained are presented in the following Table (the pH corresponds to the pH obtained during the precipitation of the compound).

TABLE 3

Comparison of the precipitation pH on oxidative catalytic activity of solids during the oxidation of benzyl alcohol to benzaldehyde.

| Entry | pH | Eq. Mn | Conversion[b] (%) | Yield[b] (%) | Selectivity[b,c] (%) |
|---|---|---|---|---|---|
| 1 | 9.5 | 1 | 70 | 69 | >99 |
| 2[d] | 9.5 | 0.3 | 22 | 21 | >99 |
| 3 | 10 | 1 | <93[e] | >54[e] | — |
| 4[d] | 10 | 0.1 | 8 | 7 | >99 |
| 5[d] | 10.5 | 0.3 | 73 | 72 | >99 |
| 6 | 11 | 1. | <86[e] | >44[e] | — |
| 7[d] | 11 | 0.3 | 79 | 78 | >99 |
| 8 (comparative) | 14 | 1 | <45[e] | >16[e] | — |
| 9[d] (comparative) | 14 | 0.3 | 10 | 9 | >99[e] |

[a]Reaction conditions: benzyl alcohol 1 (100 mmol.$L^{-1}$) catalyst, anhydrous toluene reflux at 110° C., 5 h.
[b]Conversion, yield and selectivity were determined by GC-MS, using dodecane as an internal standard.
[c]Ratio of GC-MS to aldehyde yield on conversion.
[d]Reaction performed with bubbling air. e Loss of reagents on the catalyst matrix.

The first reactions involving the compounds prepared via the method of the invention (pH=9.5) and benzyl alcohol in a stoichiometric amount show a yield of 70% benzaldehyde with excellent selectivity after 5 hours of reaction. In addition, no loss of reagent or product by retention on the mineral matrix of the compound is observed, contrary to what is observed for compounds formed at higher pH.

However, when the compounds prepared via the method of the invention (pH=9.5) are used in a catalytic amount (0.3 eq) with bubbling air to re-oxidize the catalyst using oxygen, the reaction only occurs in a stoichiometric quantity (20% conversion). The oxygen contained in the air does not allow the re-oxidation of the solids prepared at pH=9.5, 10 and 14.

On the contrary, a re-oxidation of the compounds (pH=10.5) and solid (pH=11) by the dioxygen of the air is observed. When the compounds are engaged in a catalytic amount (0.3 eq), a conversion of 73% and 79% respectively is obtained in 5 hours of reaction with a total selectivity of benzaldehyde. A 100% yield is obtained after 7 hours of reaction.

Therefore, the modification of the precipitation pH allows the synthesis of manganese oxide compounds with oxidative power much higher than that observed with compounds prepared with a precipitation pH of 14. The compounds prepared by the method of the invention shows excellent selectivity to benzaldehyde, without over-oxidation to benzoic acid. The compounds prepared at pH=11 and pH=10.5 have the particularity of being re-oxidized by oxygen in the air.

Example 4: Comparison of Activity with Synthetic and Commercial Catalysts

In order to determine the origin of the activity of the compounds prepared via the method of the invention, synthetic catalysts were prepared. Since precipitation pH influences the activity and re-oxidation of compounds through air oxygen, it is expected that calcium and/or magnesium, the main elements affected by pH change in the range 9-12, play a role in the activity of the catalysts formed.

Various synthetic catalysts have been prepared from manganese, calcium and magnesium salts.

The preparation of these catalysts was identical to that followed to synthesize the solids of the invention prepared at a pH=11 from the effluent 3. The synthetic catalysts are derived from commercial products $MnSO_4$, $CaSO_4$, $MgSO_4$. Catalysts 3, 4 and 5 of Table 4 are reconstituted so as to respect the Mn, Mg and Ca ratios of the solid of the invention obtained from effluent 3.

The concentrations of committed salts are identical to those of the effluents, except in the case of Mn-synthetic catalysts where the concentration of $MnSO_4 \cdot H_2O$ has been multiplied by 4 with respect to the concentration of manganese sulphate in the effluents so as to obtain more material to work on.

The catalytic activity of these catalysts was tested under the same conditions as for the compounds of the invention, by taking the oxidation of benzyl alcohol to benzaldehyde as a model reaction. The results are shown in Table 4.

TABLE 4

Comparison of the oxidative catalytic activity of the solids of the invention (pH = 11) with that of synthetic and commercial catalysts during the oxidation of benzyl alcohol to benzaldehyde.

| Entry | Catalyst | Eq. Mn | Conversion[b] (%) | Yield[b] (%) | Selectivity (%) |
|---|---|---|---|---|---|
| 1 | Solid according to the invention prepared at pH = 11 | 0.3 | 79% | 78% | >99% |
| 2 | Mn-synthetic | 0.3 | 100% | 99% | >99% |
| 3 | MnCa-synthetic | 0.3 | 100% | 99% | >99% |
| 4 | MnMg-synthetic | 0.3 | 67% | 66% | >99% |
| 5 | MnCaMg-synthetic | 0.3 | 90% | 89% | >99% |
| 6 | $MnO_2$ commercially activated[d] | 1 | 89% | 88% | >99% |
| 7 | $MnO_2$ commercially activated | 0.3 | 38% | 37% | >99% |

Reaction conditions: benzyl alcohol 1 (100 mmol.L$^{-1}$), catalyst, anhydrous toluene, bubbling with air, reflux at 110° C., 5 h.
[b]Conversion, yield and selectivity were determined by GC-MS, using dodecane as an internal standard.
[c]Ratio of GC-MS to aldehyde yield on conversion.
[d]Reaction performed without bubbling air.

The conversion to benzaldehyde is 100% in cases where the manganese is not coupled to any other metal as well as in the presence of calcium (Table 4, entries 2-3). The method of the invention thus makes it possible to obtain an activated manganese (IV) oxide, more active than $MnO_2$, including activated $MnO_2$. These results do not allow one to know whether the presence of calcium within the catalyst has a positive or neutral effect on its reactivity. In contrast, the presence of magnesium appears to reduce the activity of the catalyst, since the GC-MS yield decreases to 66% and 89% for the MnMg-synthetic and MnCaMg-synthetic catalysts, respectively.

In comparison, the oxidation reaction of benzyl alcohol was also tested under the same conditions with commercially activated $MnO_2$. Introduced in stoichiometric amount, the reactivity is similar to that of the compounds of the invention, with an 88% yield of benzaldehyde (Table 4, entry 6). However, when introduced in a catalytic amount, the commercially activated $MnO_2$ is not (or very little) reoxidized by the dioxygen of air, since the yield is only 37% (Table 4), entry 7). These results are in agreement with the literature data that commercially activated $MnO_2$ must be introduced in excess to effect the oxidation of organic substrates.

In conclusion, with respect to the oxidation of benzyl alcohol to benzaldehyde, the compounds of the invention (prepared at pH=11) have an oxidizing catalytic activity greater than that of commercially activated $MnO_2$. This reactivity seems intrinsic to the implemented synthetic procedure, since the Mn-synthetic catalysts show an activity greater than that of the solids of the invention (pH=11). As expected, magnesium has an antagonistic effect on the reactivity of the catalysts, but the experiments carried out do not allow one to conclude as to the effect of synergy between manganese and calcium. Therefore, the procedure employed makes it possible to form an activated manganese (IV) oxide with a high oxidizing power.

Finally, it is important to take into consideration the environmental footprint that the synthesis of Mn-synthetic catalysts involves compared to that of the compounds of the invention. In fact, the manganese sulphate used to synthesize the Mn-synthetic catalysts is generally prepared by treating $MnO_2$ with sulfur dioxide or by reacting potassium permanganate with sodium hydrogen sulphate and hydrogen peroxide. In addition to the catalytic performances, it is important to take into account the life cycle analysis (LCA) of catalysts formed so that the synthesis method is part of a sustainable development approach.

Example 5: Use of the Solids of the Invention in the Selective Oxidation of HMF (HydroxyMethylFurfural) to DFF (DiFormyl Furane)

The compounds of the invention (pH=11) were used as an oxidizing catalyst in the selective oxidation reaction of HMF to DFF.

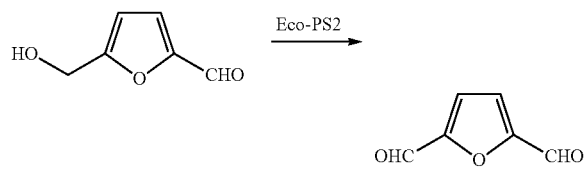

HMF (126 mg, HMF DFF 1 mmol) was dissolved in methoxycyclopentane (2 mL), the catalyst (0.3 mol eq Mn) and 10 mL of dry toluene were placed in a container. The solution was stirred and refluxed at 110° C. in the presence of bubbling air for 5 h. The solution was then acidified with an aqueous solution of sulfuric acid at pH=3.3 (10 mL). Ethyl acetate (10 mL) was added and the solution was stirred for 15 minutes. The solution was filtered and the solid was washed three times with 10 mL of ethyl acetate. The aqueous phase was extracted with three times 10 mL of ethyl acetate. The various organic phases were combined and the solvent was evaporated. An orange-yellow solid was obtained. Conversion and selectivity were determined by GC-MS, using biphenyl as the internal standard. The results are shown in Table 5.

TABLE 5

Conversion to HMF and selectivity to DFF obtained with Eco-PS2 as catalysts.

| Entry | Catalyst | Eq. Mn | Conversion b (%) | Selectivity b, c (%) |
|---|---|---|---|---|
| 1 | Solid according to the invention prepared at pH = 11 | 1 | 50% | 75% |
| 3 | Solid according to the invention prepared at pH = 11 | 0.3 | 45% | 71% |
| 3 | Solid according to the invention prepared at pH = 9.5 | 1 | 60% | 77% |

[a]Reaction conditions: HMF 3 (100 mmol.L$^{-1}$) dissolved in CPME, catalyst, anhydrous toluene, bubbling with air, reflux at 110° C., 5 h.
[b]Conversion, yield, and selectivity were determined by GC-MS, using biphenyl as an internal standard.
[c]Ratio of GC-MS to aldehyde yield on conversion.

GC-MS analyses show no other products besides HMF and DFF. The use of the compounds of the invention (pH=11) in stoichiometric or catalytic amounts gives the same results in terms of conversion and selectivity (Table 5, entry 1-2). In both cases, the conversion is close to 50%.

The conversion and the yield obtained with the solids of the invention (pH=9.5) are slightly higher than those obtained with the solids of the invention (pH=11), with 60% conversion (Table 5, entry 3). In all cases, the selectivity in DFF is close to 75%. In order to determine the presence or absence of carboxylic acids, IR and LC MS analyses confirmed the formation of HMF and DFF.

N,O-bis(trimethylsilyl) trifluoroacetamide was used as silylating agent. GC-MS analysis of the silylation products indicates the presence of no other compounds than DFF and silylated HMF. The selectivity of the reaction is therefore very high and superior to the methods of the literature which describe the formation of mono and diacids.

Example 6: Oxidation Reactions

The method of the invention has been implemented in several oxidation reactions using the catalyst from effluent 2. The results are shown in Table 6.

TABLE 6

Oxidation reactions

| Entry | Alcohol | Aldehyde | Conversion (%) |
|---|---|---|---|
| 1 | benzyl alcohol (PhCH$_2$OH) | benzaldehyde (PhCHO) | 100 |
| 2 | 1-phenylethanol (PhCH(OH)CH$_3$) | acetophenone (PhC(O)CH$_3$) | 98 |

TABLE 6-continued

Oxidation reactions

| Entry | Alcohol | Aldehyde | Conversion (%) |
|---|---|---|---|
| 3 | 3,4-dihydroxybenzyl alcohol | 3,4-dihydroxybenzaldehyde | 61 |
| 5 | furfuryl alcohol | furfural | 49 |
| 6 | cinnamyl alcohol | cinnamaldehyde | 94 (54% yield) |

The oxidation is compatible with the OH group of phenol. The primary alcohol is oxidized without touching the phenolic nucleus (entry 3). This reaction makes it possible to obtain vanillin, the product highly sought after in the food, cosmetics, perfume and other industries.

Oxidation does not degrade the furan nucleus (entries 4 and 5). The reaction stops at the dialdehyde. No trace of acid or diacid is observed either in GC/MS or after treatment of the medium with an inorganic acid followed by extraction. Dialdehyde is a very interesting biosourced building block (see J. Ma, Z. Du, J. Xu, Q Chu, Y. Pang ChemSusChem, 2011, 4, 51-54, A. Gandini, Green Chem., 2011, 13, 1061-1083).

Cinnamic alcohol is almost completely oxidized to the corresponding aldehyde (entry 6). The aldehyde product is isolated with 54% yield and 40% condensation product is obtained as a reaction by-product. Cinnamic aldehyde is a highly sought-after product in the food, cosmetics, perfume and other industries. The advantages of this method over existing methods are as follows:

- the reaction is effected at atmospheric pressure
- it is not necessary to bubble pure oxygen or to make the reaction under pressure of $O_2$. Our method works either in air or by bubbling the air into the reaction medium.
- the amount of manganese used in the reaction is from 10 mol % to 50 mol % in Mn, which is much lower than the existing methods.

Example 7: Oxidative Cleavage

The method may also be extended to the oxidative cleavage of α-diols, α-hydroxyketones, α-hydroxyacids. The results are shown in Table 8.

TABLE 8

Oxidative cleavage using the catalyst from effluent 2

| Entry | Alcohol | % Benzaldehyde | Conversion |
|---|---|---|---|
| 1 | 1-phenyl-1,2-ethanediol | 100% | 100% |
| 2 | hydrobenzoin | 84% | 100% |
| 3 | mandelic acid | >95 | >95% |

The advantages of this method are as follows:
- the preparation of the catalyst requires a small amount of sodium hydroxide or other base.
- no base used during the reaction
- no need to bubble pure oxygen or make the reaction under pressure in the pure oxygen atmosphere. Our method works either in air or by bubbling air into the reaction medium
- the reaction is carried out at atmospheric pressure and with small amounts of Mn

Example 8: Epoxidation of Alkenes

The epoxidation of the alkenes may also be easily carried out from the industrial effluent in the presence of a cooxidant such as hydrogen peroxide. The method may be advantageously compared to the methods of the literature.

General Procedure for the Epoxidation Reaction:

NaHCO$_3$ (0.007 g, 0.09 mol, 5 eq), effluent 2 (0.26 mL (pH=3.5, Mn=12 ppm), 0.001 eq relative to Mn), t-BuOH or DMF (0.263 mL) and alkene (0.02 mol, 1 eq) at 30° C. in air. After stirring for 10 minutes, 30% H$_2$O$_2$ (0.016 mL, 0.17 mol, 10 eq) is added to the reaction mixture at 30° C. in air. The evolution of gas is observed after one minute. Stirring is continued for another four hours and then the reaction is cooled to room temperature. The product is extracted with dichloromethane and analyzed by GC MS.

The conversions are shown in Table 8.

TABLE 8

Epoxidation of alkenes

| Substrate | Eco-PS2/ tBuOH | Eco-PS2/DMF | EcoMn** (DMF) | literature |
|---|---|---|---|---|
| Styrene | 91% | — | 91% | |
| Cyclooctene | 81% | — | 55% | |
| Cyclohexene | 86% | — | 89% | |
| Isoeugenol | 0% | 50%* | Oxidative cleavage | |
| Pinene | traces | 100% | 75% | 40% (Qi, B. *J. Mol. Cat. A* 2010, 322, 73) |
| Limonene | traces | 92% | 43% | |
| Linalool | traces | 95% | 63% | |
| Nopol | traces | 45% | 74% | |

*In the case of isoeugenol, GC-MS indicates the formation of a family of isoeugenol self-condensation products. The majority product appears to be Licarine A.
**Eco-Mn derived from Mn accumulators of the genus Grevillea The Eco-PS2 solids represent the catalysts prepared via the method of the invention.

The invention claimed is:

1. Method for the preparation of a solid material comprising manganese, said method comprising the following steps:
    a. bringing into contact an aqueous effluent comprising manganese, with an agent capable of oxidizing manganese, and obtaining an aqueous solution comprising oxidized manganese;
    b. adding to the aqueous solution comprising oxidized manganese obtained at the end of step a) of a base until a pH of between 9.5 and 12, and obtaining a solution comprising a precipitate that comprises manganese;
    c. filtration of the solution obtained at the end of step b); and
    d. obtaining a solid material comprising manganese.

2. Method according to claim 1, wherein the solid material obtained at the end of step d) comprises oxides of manganese.

3. Method according to claim 1, wherein the agent capable of oxidizing manganese is chosen from hydrogen peroxide, dioxygen or sodium percarbonate.

4. Method according to claim 1, wherein the agent capable of oxidizing manganese is added in a concentration of between 0.015 mL/L and 2 mL/L.

5. Method according to claim 1 wherein the base is selected from potassium hydroxide, sodium hydroxide, calcium carbonate, sodium carbonate and calcium hydroxide.

6. Method according to claim 1 wherein the effluent further comprises one or more of the elements selected from aluminum, calcium, copper, iron, potassium, magnesium, sodium, zinc, nickel, arsenic and silicon.

7. The method of claim 1, wherein:
    the step of bringing into contact the aqueous effluent comprises at least 5 mg/L of manganese, with an agent capable of oxidizing manganese, at a temperature between 10° C. and 50° C.;
    the step of adding to the aqueous solution comprising oxidized manganese a base is performed until a pH greater than 9.5 is achieved; and
    the solid material obtained is manganese (IV) and/or Mn (III).

8. Method according to claim 1, wherein the agent capable of oxidizing manganese is hydrogen peroxide.

9. Method according to claim 1 wherein the base is sodium hydroxide.

10. Method according to claim 1 wherein in step b) the base is added until a pH 9.5 is obtained.

11. Method according to claim 1 wherein the effluent further comprises one or more of the elements selected from aluminum, calcium, copper, iron, potassium, magnesium and sodium.

12. Method of carrying out an organic synthesis reaction comprising the following steps:
    i) preparing a solid material comprising manganese according to claim 1;
    ii) carrying out an organic synthesis reaction by contacting the solid material comprising manganese obtained at the end of stage i) as a catalyst with a reaction medium.

13. Method according to claim 12, in which the organic synthesis reaction is chosen from
    the oxidation reactions;
    the oxidative cleavage reactions; and
    the epoxidation reactions of alkenes.

14. Method according to claim 13, wherein the organic synthesis reaction is carried out in the presence of ambient oxygen.

15. Method according to claim 12, in which the organic synthesis reaction is chosen from
    the reactions for the oxidation of alcohols to aldehydes or ketones, said alcohols being selected from alcohols in alpha of an aromatic ring, in alpha of heterocyclic, in alpha of a double bond, and aliphatic alcohols;
    the oxidative cleavage reactions of diols, of alpha hydroxy acids, of alpha hydroxylated carbonyl derivatives, of dicarbonyl derivatives; and
    the epoxidation reactions of mono, di-, tri or tetrasubstituted alkenes.

* * * * *